United States Patent [19]

Otto et al.

[11] 4,285,698
[45] Aug. 25, 1981

[54] ANALYSIS OF AFLATOXINS IN PEANUTS BY HIGH PRESSURE LIQUID CHROMATOGRAPH

[75] Inventors: Susan E. Otto, Fenton; David L. Dunmire, St. Louis, both of Mo.

[73] Assignee: Peanut Research & Testing Laboratories, Inc., Edenton, N.C.

[21] Appl. No.: 144,681

[22] Filed: Apr. 28, 1980

[51] Int. Cl.$^3$ ...................... G01N 33/02; G01N 31/08
[52] U.S. Cl. .............................. 23/230 B; 23/230 R; 23/230 M
[58] Field of Search ............. 23/230 R, 230 B, 230 M

[56] References Cited

PUBLICATIONS

Chemical Abstracts, 79: 101193(b), (1973).
Chemical Abstracts, 82: 107062s, (1975).
Chemical Abstracts, 88: 87719e, (1978).

*Primary Examiner*—Ronald Serwin
*Attorney, Agent, or Firm*—Morse, Altman, Oates & Dacey

[57] ABSTRACT

A method is disclosed for quickly and easily determining the presence and concentration of aflatoxins in peanuts. Aflatoxins are extracted from ground peanuts with a methanol-water solution using a tissuemizer. The extracted sample is filtered and an aliquot of the filtrate is transferred to a separatory funnel. A salt solution is added to remove interferences. The combined aqueous solution is then extracted with dichloromethane. The dichloromethane extract is evaporated to dryness, trifluoroacetic acid is then added and the resulting residue taken up in the mobile phase. The solution is then passed through a minicolumn for filtration and final cleanup. An aliquot is then injected into a high pressure liquid chromatograph system for separation of the four aflatoxin components, B1, B2, G1 and G2. Quantitation is done using a filter fluorescence detector.

8 Claims, 6 Drawing Figures

ANALYSIS OF AFLATOXINS IN PEANUTS BY HIGH PRESSURE LIQUID CHROMATOGRAPH

BACKGROUND OF THE INVENTION

1. Field of the Invention

This invention relates generally to the quantitative and qualitative detection of aflatoxins in peanuts and more particularly is directed towards a new and improved method for analyzing aflatoxins in peanuts by means of high pressure liquid chromatography.

2. Description of the Prior Art

Aflatoxin is a known carcinogen that enters food as a consequence of the manner in which foods are grown, handled or stored. Aflatoxin is not a deliverate food additive but occurs as a natural contaminant in such common foods as peanuts and corn.

Aflatoxin is a generic term referring to a group of highly toxic compounds produced by the fungus *Aspergillus flavus/parasiticus*. In additional to the original recognition of aflatoxins B1, B2, G1 and G2, there also have been a large number of metabolites whose structures have been examined. These are mostly produced in mammalian tissue upon ingestion by the mammal of the parent compound B1, although some may also be produced by the fungus or by chemical treatment of B1. Of the four original aflatoxins, B1 is the most common, usually comprising about 90% of the aflatoxin residue observed on contaminated foodstuffs and it is also the most toxic. The biological activity of aflatoxin B1 is relatively similar to the other aflatoxins.

In order to detect the presence of aflatoxins on food products such a peanuts, it is common practice to run regular tests on samples of peanuts as a quality control function. However, the present methodology is quite long, typically running about two and one-half hours to complete and is characterized by a sensitivity in the 3-5 ppb range. In food processing operations the long analysis time is unsatisfactory since testing must be carried out prior to processing of a batch of nuts. It would be far more desirable to have a capability of making frequent tests on an on-going basis so that testing can be carried out more or less simultaneously with the food processing operations such as blanching, roasting, and the like.

Accordingly, it is an object of the present invention to provide a new and improved method for testing peanuts for the presence of aflatoxins.

Another object of this invention is to provide a new and improved method for quickly and efficiently analyzing peanuts and the like for the presence of aflatoxins by means of high pressure liquid chromatography.

Still a further object of this invention is to provide a process for detecting aflatoxins in peanuts in a reliable and precise manner that can be carried out on an on-going basis.

SUMMARY OF THE INVENTION

This invention features the method of testing peanuts and the like for aflatoxin, comprising the steps of extracting any aflatoxins present in a sample of ground peanuts or peanut butter with a methanol-water solution using a tissuemizer. The extracted sample is then filtered and an aliquot of the filtrate is then transferred to a separatory funnel. Interferences are removed by adding a salt solution. The combined aqueous solution is then extracted with dichloromethane. The dichloromethane extract is then evaporated to dryness, trifluoroacetic acid is added and the resulting residue is taken up in the mobile phase. The solution is then passed through a minicolumn for filtration and final cleanup. The aliquot is then injected into the high pressure liquid chromatograph system for separation of the four aflatoxin components B1, B2, G1, and G2. Quantitation is carried out using a fluorescence detector. The addition of the trifluoroacetic acid catalyzes the hydration of the double bond in the B1 and G1 components to form the hemiacetal, which fluoresces at a higher intensity.

DETAILED DESCRIPTION OF THE PREFERRED EMBODIMENT

Figure 5:
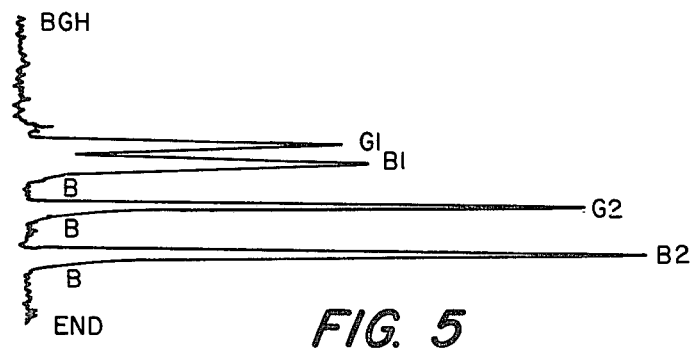
FIG. 5 is a graphical display representing a printout of a high pressure liquid chromatograph showing aflatoxin concentrations using the present process, and, FIG. 6 is a flow diagram of the process.
Figure 1:
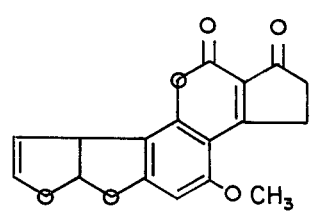
FIG. 1 is a diagram representing the chemical structure of aflatoxin B1.
Figure 2:
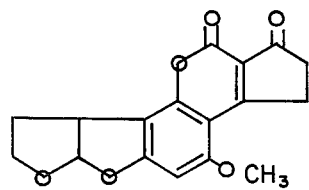
FIG. 2 is a diagram representing the chemical structure of aflatoxin B2.
Figure 3:
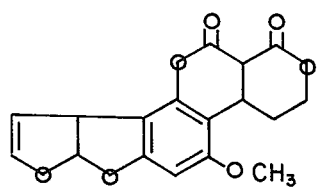
FIG. 3 is a diagram representing the chemical structure of aflatoxin G1.
Figure 4:
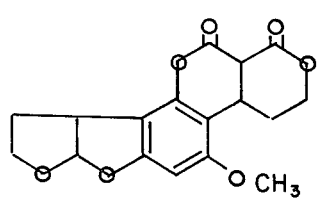
FIG. 4 is a diagram representing the chemical structure of aflatoxin G2.
Figure 6:
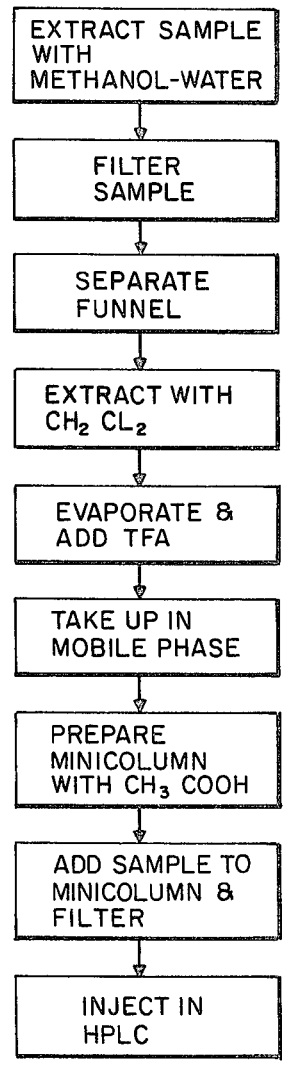

The analytical procedure disclosed herein may be advantageously used in a food processing operation such as a processing plant adapted to roast and/or blanch peanuts. Typically, a plant of this type will receive shelled nuts in bulk quantities and, after being initially stored in bins for a relatively short period time, they are cleaned and passed through roasting ovens. After roasting the nuts are fed into blanching machines, cleaned and then sorted to remove unblanched nuts or other rejects. In such a plant, samples of nuts may be removed at different stages; first prior to entry into the storage bins when first unloaded, next after the cooling stage of the roasting operation, directly after the blanching operation and then again final samples may be collected after the nuts have been sorted. The various samples are collected and analyzed in accordance with the present procedure to be described below. Preferably the procedures are carried on continuously in order to provide current information on the level of aflatoxins in the peanuts then in process. By having available current information for work in process with respect to the aflatoxin level, corrective steps can be immediately taken in the event aflatoxin levels exceed an acceptable concentration. In practice, aflatoxin may be present in trace amounts in any given load of peanuts and as a practical matter it is not possible to remove totally all aflatoxins from peanuts or other foods. However, using the combination of both automatic and manual sorting procedures and other techniques, the amount of aflatoxin present can be reduced to a negligible amount such as something on the order of less than 5 ppb.

The following is a detailed description of the procedure for analyzing samples of peanuts in accordance with the present invention. It has been found convenient to use peanuts that are ground to a peanut meal or paste and analyze in samples of 50 grams each. The 50 gram sample of ground peanuts or peanut butter is placed in a 250-ml centrifuge bottle. Any aflatoxins present in the sample are extracted from the sample by means of a methanol-water solution. This is done by adding 100 mls of a 80/20 methanol-water (MeOH/H$_2$O) extraction solution to the 250-ml centrifuge bottle. It has been found that the addition of approximatly 5 g cupric carbonate added to the sample solution is effective in removing interferences from the sample solution. Next, the sample, the methanol water-solution and the cupric carbonate are well mixed. This may be done by placing the bottle with the foregoing components on a tissuemizer which has been prepared by prewashing it with water. The tissuemizer is in the nature of a high speed blender and mixing the above for a period of one minute at high speed will throughly mix the components. The resulting mix is a greenish slurry which is then filtered. The filtering is conveniently carried out by pouring the same into a funnel lined with a filter paper such as a Whatman #1 or #4 filter paper. The filter is collected in a 50 ml graduated cylinder and, typically about a 30.0 ml aliquot is collected by the filtering process. A greenish residue remaining in the filter may then be discarded. The liquid filtrate which has been removed from the slurry is then transferred to a separatory funnel at which time 40-50 mls salt solution, preferably zinc acetate, are added in the funnel. The salt solution is provided for removing interferences from the solution. The liquid aliquot and the salt solution are then swirled gently in order to mix them.

Two 5-ml portions of CH$_2$CL$_2$ are extracted from the aqueous solution. The dichloromethane is drawn off twice from the bottom and fresh dichloromethane is added from the top to separate out the aflatoxin from the aqueous solution. Aflatoxins are more soluble in dichloromethane than in the aqueous solution and therefore can be drawn off the bottom of the separator. The aqueous solution which remains in the upper portion of the separator funnel is discarded once the dichloromethane at the bottom of the funnel is drawn off as described above. The two CH$_2$CL$_2$ extracts are then combined in a conical centrifuge tube. The above order of solution is critical for efficiency of extraction and for reducing the incidence of emulsion formation.

The now combined CH$_2$CL$_2$ extracts are placed in an evaporator to dry off the liquids and to produce a near dry residue. Preferably, this is carried out under N2 with a water bath at a temperature of approximately 60° C. Next, trifluoroacetic acid (TFA) is added to make a derivative of the aflatoxins B1 and G1 which will fluoresce more strongly than would otherwise be the case. This is done by removing the residue from the evaporator, adding 500 ul of TFA to each centrifuge tube and placing them on a Vortex mixer, or the like, for 15 to 20 seconds. The TFA is then evaporated to dryness under N2 with a water bath at approximately 60° C. It is critical at this point that all excess TFA be evaporated.

The mobile phase is a 20/80 solution of THF/(1% CH$_3$COOH), both components filtered twice prior to being mixed together. The method of preparation involves adding 800 mls of 1% CH$_3$COOH (10 mls CH$_3$COOH diluted to 1 L with H$_2$O) to a 1 L volumetric flask and dilute to volume with THF. Each portion of the mobile phase must be twice filtered through an appropriate filtering medium, preferably a 0.5 micron filter, prior to mixing with THF. The mobile phase is degassed by bubbling helium through it prior to placing it in a high pressure liquid chromatograph and continuously degas the same by stirring it slowly with a magnetic stirrer, preferably using a teflon-coated stirring bar.

Next, the residue remaining from the TFA evaporation step is taken up in 3.0 mls mobile phase and mixed in a Vortex. A minicolumn bed is then prepared allowing approximately 1 ml of 1% CH$_3$COOH to drain through. In practice, the minicolumns employed at this stage are glass tubes 11" long×6 mm outside diameter with a ½" taper. A glass wool plug is used and is packed with 2" Bondapak C18/Porasil B. 2-ml disposable serological pipettes may be used in place of plain glass tubes. Silanized glass wool is available from Applied Science Labs, State College, Pa. 16801, and Bondapak, C18/Porasil B is available from Waters Associates.

Next, a 1 ml sample solution is added to the minicolumn. This is allowed to drain and then discarded. Next, the remaining sample solution is added to the minicolumn and collected in a WISP vial. At this stage the eluate should be clear, but not necessarily colorless. The vial is then placed in a high performance liquid chromatograph through an injector. In order to maintain a continuous analysis using a large number of samples, an automatic injector is preferred. It has been found that a model 710A WISP automatic sample processor from Waters Associates has provided very satisfactory results. The processor involves a rotating carousel-like wheel on the periphery of which is mounted a large number of vials containing separate samples for processing. As the wheel is indexed, the sample is withdrawn automatically from each vial and injected into the liquid chromatograph. The liquid chromatograph for this purpose may be a model ALC/GPC high pressure liquid chromatograph equipped with a model 6000A pump and a model U6K injector available from Waters Associates Inc. Milford, Mass. The chromatograph is equipped with a model 420 fluorescence detector with an excitation filter of 365 nm and an emission filter of 425 nm, also available from Waters Associates. Various recorders can be employed although a Varian Model 9176 dual pen recorder, 10 mv/FS available from Varian, Walnut Creek, Calif., has provided satisfactory performance.

Fluorometry is both a quantitative and qualitative measurement technique utilizing the phenomenon of fluorescence in which a long wave length light is emitted from a sample which has absorbed light of a shorter wave length. A fluorescent lamp provides the light to excite fluorescence in the sample. The light from this lamp is directed through the excitation filter which transmits selected wavelengths of light to the sample in the flow cell of the chromatograph. The emission filter is selected to transmit only a particular band of fluorescence. A photo multiplier tube is employed to detect the fluorescent signal emitted from the sample and convert it into an electrical signal proportional to the magnitude of fluorescence of the sample.

In the practice of the foregoing process, it has been found that the described procedure will detect 0.25 ppb of each aflatoxins B1, B2, G1 and G2 for a detection level of 1.00 ppb total aflatoxin or greater. The minimum detectable peak is determined on a signal-to-noise ratio=5. Sensitivities may be increased by the use of sample concentration, increased attenuation, larger injection volume and/or lower standard concentration.

The high pressure liquid chromatographic system in the preferred practice of the invention is operated under the following conditions:

| | |
|---|---|
| Column: | Zorbax ODS 25 cm × 4.6 mm i.d. |

-continued

| | |
|---|---|
| Mobile Phase: | 20/80 THF/ (1% CH₃COOH) |
| Flow Rate: | 1.0 ml/min |
| Pressure will be approximately 2000 psi | |
| Temperature: | Ambient (ca 25° C.) |
| Detector: | Fluorescense model 420 with an excitation filter 365nm and an emission filter 425 nm |
| Gain: | 32 |
| Span: | maximum |
| Adjust | zero when system conditions have stabilized |
| Recorder: | 10 mv/FS × 1<br>0.5 cm/min chart speed |
| WISP: | Run time 10 minutes<br>Injections/vial 1<br>Injection volume:<br>a. 100 ng/ml standard-25ul<br>b. 50 ng/ml standard-25ul<br>c. 10 ng/ml standard-100 ul<br>d. Unknown sample or low level sample-100 ul<br>e. High level sample - as needed |

The practice aflatoxin standards are injected followed by the samples being tested. The aflatoxin standards should be reinjected at the end of the run and/or after every ten samples to monitor any changes in retention times, peak height responses, and separation factors. In carrying out the procedure it is good practice to measure and record the retention time and peak heights of all standards. In this process the aflatoxins are eluted in the following order: G1 (as G2a), B1 (as B2a), G2 and B2. The retention times of sample peaks are measured and recorded. Aflatoxin components are identified by comparison with the retention times of the standards.

Individual aflatoxins standards of fine quality are commercially available from suppliers such as Applied Science Laboratories. Each component, namely B1, B2, G1 and G2, is prepared separately as follows: first of all the dry standard (approximately 4 mg or by the suppliers instructions) is dissolved in sufficient benzene/acetonitrile (98/2) to obtain approximately 1 mg/ml concentration to provide the master solution. Next, an aliquot of the master solution is diluted in an appropriate volumetric flask to sufficient volume with benzene/acetonitrile (98/2) to obtain approximately 3 ug/ml concentration to provide the stock solution. Next, each stock solution is read on a UV spectrophotometer set at 350 nm and the readings in the absorbance units are recorded. The exact concentrations are then calculated using the extinction coefficients as follows:

Calculation formula:

$$\frac{(A)(MW)(1000)}{E} = \text{concentration in ug/ml or ng/ul}$$

where:
A = Absorbance units
MW = Molecular weight
E = Extinction coefficient in benzene/acetonitrile (98/2)

| Aflatoxin | MW | E |
|---|---|---|
| B1 | 312 | 19,800 |
| B2 | 314 | 20,900 |
| G1 | 328 | 17,100 |
| G2 | 330 | 18,200 |

Example:

Absorbance reading on B1 = 0.283
Stock B1 = (0.283) (312) (1000)/19,800 = 4.45 ug/ml Using the calculated concentrations, three combined standards are prepared in benzene such that the concentration of each component is approximately 100 ng/ml, 50 ng/ml, 10 ng/ml.

Example:

| | |
|---|---|
| B1 | 4.45 ng/nl |
| B2 | 1.88 ng/nl |
| G1 | 2.76 ng/nl |
| G2 | 4.17 ng/nl |

100 ng/ml combined standard (single 25 ml volumetric)
B1 (600 ul) (4.45 ng/ul)/25 ml = 106.8 ng/ml
B2 (1500 ul) (1.88 ng/ul)/25 ml = 112.8 ng/ml
G1 (1000 ul) (2.76 ng/ul)/25 ml = 110.4 ng/ml
G2 (600 ul) (4.17 ng/ul)/25 ml = 100.1 ng/ml These provide the working standards which are to be injected with the samples into the high pressure liquid chromatograph. The aflatoxin standards typically are stable for less than 24 hours when in a methanol solution, even when refrigerated. However, the aflatoxin standards are stable for several months when in a benzene or benzene/acetonitrile (98/2) solution. For increased stability, all standard solutions should be kept refrigerated, but allowed to warm to room temperature prior to using the same. An aliquot of each of the three working standard solutions should be taken through the derivatization step along with the samples. The derivatized standards are also taken through the minicolumn procedure along with the samples.

The incidence of aflatoxin, calculated in parts per billion, (ppb), can be derived by the following calculation:

$$\text{Aflatoxin, ppb} = \left(\frac{Vi\,1}{Vi}\right)\left(\frac{PH}{PH\,1}\right)(C)\left(\frac{Ve}{W}\right)\left(\frac{Vf}{Va}\right)$$

Where
Vi 1—injection volume, standard (ul)
Vi—injection volume, sample (ul)
PH—peak height, sample (cm)
PH1—peak height, standard (cm)
C—standard concentration (ng/ml)
Ve—volume extraction solution (ml)
W—weight sample, (g)
Vf—final volume, sample (ml)
Va—volume of aliquot, sample (ml)

Example:

$$\text{Aflatoxin } B1 \left(\frac{100\ ul}{100\ ul}\right)\left(\frac{6.1\ cm}{7.1\ cm}\right)(10.7\ ng/ml)\left(\frac{100\ mls}{52.5\ g}\right)\left(\frac{3\ mls}{30\ mls}\right) = 1.75\ ng/g = 1.75\ ppb\ \text{Aflatoxin } B1$$

While the invention has been described with particular reference to the illustrated embodiment, numerous modifications will appear to those skilled in the art.

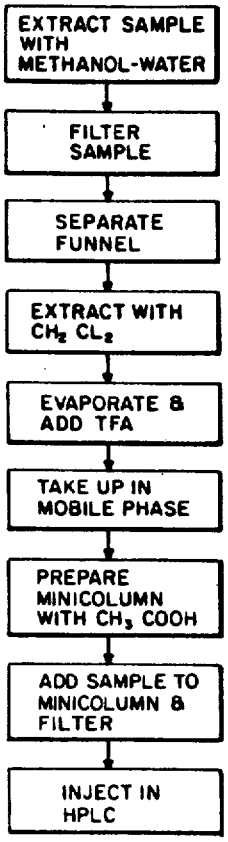

Having thus described the invention, what we claim and desire to obtain by Letters Patent of the United States is:

1. The method of analyzing peanuts and the like for the presence of aflatoxins, comprising the steps of
    (a) grinding a quantity of said nuts into a paste,
    (b) mixing said paste with a solution of methanol and water to form a slurry therefrom,
    (c) filtering said slurry to extract a filtrate therefrom in the form of an aqueous solution,
    (d) mixing said aqueous solution with a quantity of dichloromethane,
    (e) extracting said dichloromethane from said aqueous solution to obtain an extract therefrom,
    (f) evaporating the dichloromethane from said extract to obtain a first residue therefrom
    (g) mixing said first residue with a quantity of trifluoracetic acid to form a derivative of said aflatoxins,
    (h) evaporating said trifluoracetic acid to obtain a second residue therefrom,
    (i) mixing said second residue with a solution of tetrahydrofuran and $CH_3COOH$ to obtain a mobile phase therefrom,
    (j) filtering said mobile phase through a minicolumn,
    (k) injecting said mobile phase into a high pressure liquid chromatograph to separate the aflatoxin components in said mobile phase, and,
    (l) measuring the concentrations of each of said components.

2. The method of claim 1 wherein said solution of methanol and water comprises approximately 80% methanol and 20% water by volume.

3. The method of claim 1 including the step of adding a salt solution to said filtered slurry.

4. The method of claim 3 wherein said salt solution is zinc acetate.

5. The method of claim 1 wherein said mobile phase comprises approximately 20% tetrahydrofuran and 80% (1% $CH_3COOH$) by volume.

6. The method of claim 1 wherein said concentrations are measured by exposure thereof to a fluorescing light source to excite fluorescence in said components and detecting and measuring selected bands of fluorescence therefrom.

7. The method of claim 1 including the step of injecting into said chromatograph aflatoxin standards in the mobile phase to obtain reference data therefrom.

8. The method of claim 1 wherein said minicolumn is a glass tube having an inside diameter of approximately 4 mm I.D. and containing a filter material therein.

* * * * *

UNITED STATES PATENT AND TRADEMARK OFFICE
CERTIFICATE OF CORRECTION

PATENT NO. : 4,285,698

DATED : August 25, 1981

INVENTOR(S) : Susan E. Otto et al.

It is certified that error appears in the above—identified patent and that said Letters Patent is hereby corrected as shown below:

The title page should be deleted to appear as per attached title page.

Signed and Sealed this

Fifth Day of January 1982

[SEAL]

Attest:

*Attesting Officer*

GERALD J. MOSSINGHOFF

*Commissioner of Patents and Trademarks*

United States Patent [19]

Otto et al.

[11] 4,285,698

[45] Aug. 25, 1981

[54] ANALYSIS OF AFLATOXINS IN PEANUTS BY HIGH PRESSURE LIQUID CHROMATOGRAPH

[75] Inventors: Susan E. Otto, Fenton; David L. Dunmire, St. Louis, both of Mo.

[73] Assignee: Peanut Research & Testing Laboratories, Inc., Edenton, N.C.

[21] Appl. No.: 144,681

[22] Filed: Apr. 28, 1980

[51] Int. Cl.³ .................... G01N 33/02; G01N 31/08
[52] U.S. Cl. ........................... 23/230 B; 23/230 R; 23/230 M
[58] Field of Search ............ 23/230 R, 230 B, 230 M

[56] References Cited
PUBLICATIONS

Chemical Abstracts, 79: 101193(b), (1973).
Chemical Abstracts, 82: 107062s, (1975).
Chemical Abstracts, 88: 87719e, (1978).

*Primary Examiner*—Ronald Serwin
*Attorney, Agent, or Firm*—Morse, Altman, Oates & Dacey

[57] ABSTRACT

A method is disclosed for quickly and easily determining the presence and concentration of aflatoxins in peanuts. Aflatoxins are extracted from ground peanuts with a methanol-water solution using a tissuemizer. The extracted sample is filtered and an aliquot of the filtrate is transferred to a separatory funnel. A salt solution is added to remove interferences. The combined aqueous solution is then extracted with dichloromethane. The dichloromethane extract is evaporated to dryness, trifluoroacetic acid is then added and the resulting residue taken up in the mobile phase. The solution is then passed through a minicolumn for filtration and final cleanup. An aliquot is then injected into a high pressure liquid chromatograph system for separation of the four aflatoxin components, B1, B2, G1 and G2. Quantitation is done using a filter fluorescence detector.

8 Claims, 6 Drawing Figures